(12) United States Patent
Mishra

(10) Patent No.: US 8,163,277 B2
(45) Date of Patent: Apr. 24, 2012

(54) KITS FOR TREATING DYSFUNCTION OF CARDIAC MUSCLE

(76) Inventor: Allan Mishra, Menlo Park, CA (US)

( * ) Notice: Subject to any disclaimer, the term of this patent is extended or adjusted under 35 U.S.C. 154(b) by 1419 days.

(21) Appl. No.: 11/494,166

(22) Filed: Jul. 27, 2006

(65) Prior Publication Data

US 2006/0263407 A1 Nov. 23, 2006

Related U.S. Application Data

(63) Continuation of application No. 10/941,124, filed on Sep. 15, 2004, now Pat. No. 7,314,617, which is a continuation of application No. 10/412,821, filed on Apr. 11, 2003, now Pat. No. 6,811,777.

(60) Provisional application No. 60/372,682, filed on Apr. 13, 2002.

(51) Int. Cl.
*A01N 63/00* (2006.01)
*A61M 37/00* (2006.01)

(52) U.S. Cl. .................................. 424/93.72; 604/6.02

(58) Field of Classification Search ........................ None
See application file for complete search history.

(56) References Cited

U.S. PATENT DOCUMENTS

| | | | |
|---|---|---|---|
| 4,663,289 A | 5/1987 | Veech | |
| 4,931,395 A | 6/1990 | Griffin | |
| 5,079,236 A | 1/1992 | Drizen et al. | |
| 5,124,316 A | 6/1992 | Antoniades et al. | |
| 5,147,776 A | 9/1992 | Koerner, Jr. | |
| 5,165,938 A | 11/1992 | Knighton | |
| 5,178,883 A | 1/1993 | Knighton | |
| 5,385,937 A | 1/1995 | Stamler et al. | |
| 5,403,272 A | 4/1995 | Deniega et al. | |
| 5,449,688 A | 9/1995 | Wahl et al. | |
| 5,474,891 A | 12/1995 | Murphy | |
| 5,494,590 A | 2/1996 | Smith et al. | |
| 5,510,102 A | 4/1996 | Cochrum | |
| 5,578,565 A | 11/1996 | Chao et al. | |
| 5,585,007 A | 12/1996 | Antanavich et al. | |
| 5,599,558 A | 2/1997 | Gordinier et al. | |
| 5,614,204 A | 3/1997 | Cochrum | |
| 5,643,786 A | 7/1997 | Cohen et al. | |
| 5,788,662 A | 8/1998 | Antanavich et al. | |
| 5,834,418 A | 11/1998 | Brazeau et al. | |
| 5,905,142 A | 5/1999 | Murray | |
| 5,935,850 A | 8/1999 | Clark et al. | |
| 6,098,631 A | 8/2000 | Holoshitz et al. | |
| 6,120,520 A | 9/2000 | Saadat et al. | |
| 6,183,442 B1 | 2/2001 | Athanasiou et al. | |
| 6,210,976 B1 | 4/2001 | Sabbadini | |
| 6,214,338 B1 | 4/2001 | Antanavich et al. | |
| 6,242,594 B1 | 6/2001 | Kelly | |
| 6,280,473 B1 | 8/2001 | Lemperle et al. | |
| 6,306,171 B1 | 10/2001 | Conzemius | |
| 6,315,992 B1 | 11/2001 | Noh et al. | |
| 6,322,785 B1 | 11/2001 | Landesberg et al. | |
| 6,432,119 B1 | 8/2002 | Saadat | |
| 6,447,443 B1 | 9/2002 | Keogh et al. | |
| 6,454,804 B1 | 9/2002 | Ferree | |
| 6,712,851 B1 | 3/2004 | Lemperle et al. | |
| 6,811,777 B2 | 11/2004 | Mishra | |
| 6,905,612 B2 | 6/2005 | Dorian et al. | |
| 2001/0031978 A1 | 10/2001 | Kipke et al. | |
| 2002/0006437 A1 | 1/2002 | Grooms et al. | |
| 2002/0032155 A1 | 3/2002 | Ferree | |
| 2002/0058030 A1 | 5/2002 | Monroy et al. | |
| 2002/0082220 A1 | 6/2002 | Hoemann et al. | |
| 2003/0116512 A1 | 6/2003 | Delbert Antwiler et al. | |
| 2003/0152639 A1 | 8/2003 | Britton et al. | |
| 2003/0175248 A1 | 9/2003 | Uhr | |
| 2003/0185812 A1 | 10/2003 | Ferree | |
| 2003/0192554 A1 | 10/2003 | Ferree | |
| 2003/0205538 A1 | 11/2003 | Dorian et al. | |
| 2003/0236573 A1 | 12/2003 | Evans et al. | |
| 2004/0126885 A1 | 7/2004 | Cines et al. | |
| 2004/0182795 A1 | 9/2004 | Dorian et al. | |
| 2004/0220101 A1 | 11/2004 | Ferree | |
| 2004/0220102 A1 | 11/2004 | Ferree | |
| 2004/0244806 A1 | 12/2004 | Ferree | |
| 2005/0043738 A1 | 2/2005 | Ryan | |
| 2005/0064042 A1 | 3/2005 | Vunjak-Novakovic et al. | |
| 2005/0186193 A1 | 8/2005 | Mishra | |
| 2006/0029578 A1 | 2/2006 | Hoemann et al. | |
| 2006/0041243 A1 | 2/2006 | Nayak et al. | |
| 2006/0127382 A1 | 6/2006 | Mishra | |
| 2006/0235306 A1 | 10/2006 | Cotter et al. | |
| 2006/0263407 A1 | 11/2006 | Mishra | |
| 2007/0014784 A1 | 1/2007 | Nayak et al. | |
| 2007/0037737 A1 | 2/2007 | Hoemann et al. | |
| 2007/0042016 A1 | 2/2007 | Nayak et al. | |
| 2007/0110737 A1 | 5/2007 | Mishra | |
| 2007/0122906 A1 | 5/2007 | Mishra | |
| 2007/0172472 A1 | 7/2007 | Nayak | |
| 2007/0202093 A1 | 8/2007 | Brooks et al. | |

FOREIGN PATENT DOCUMENTS

EP 0 142 339 5/1985

(Continued)

OTHER PUBLICATIONS

Paques et al., "Effect of Autologous Platelet Concentrate in Surgery for Idiopathic Macular Hole", Ophthalmology 106 (5) : 932-938 (1999).*

(Continued)

*Primary Examiner* — Sandra Saucier

(74) *Attorney, Agent, or Firm* — Knobbe, Martens, Olson & Bear, LLP

(57) ABSTRACT

Kits are described for the treatment of acute or chronic dysfunction of cardiac muscle. The kit includes a platelet-rich plasma composition with a pH adjusting agent and a catheter or syringe for delivery of the platelet-rich plasma composition to dysfunctional cardiac muscle. The kit may also include a syringe for withdrawing blood from a patient and a centrifuge device to obtain platelet-rich plasma.

8 Claims, 2 Drawing Sheets

FOREIGN PATENT DOCUMENTS

| EP | 0 417 818 | 3/1991 |
|---|---|---|
| JP | 5-500516 | 2/1993 |
| WO | WO 91/04035 | 4/1991 |
| WO | WO 00/01427 | 1/2000 |
| WO | WO 00/12018 | 3/2000 |
| WO | WO 03/015800 | 2/2003 |
| WO | WO 2004/022078 | 3/2004 |
| WO | WO 2005/065242 | 7/2005 |

OTHER PUBLICATIONS

Gehring et al., "Preparation of autologous platelets for the opthalmologic treatment of macular holes", Transfusion 39 : 144-148 (1999).*

Feuerstein, et al. "Congestive Heart Failure and Genomic Medicine: A Look Into the 21$^{st}$ Century," *Cardiovascular Drugs and Therapy*, vol. 11, No. 6, pp. 713-717, 1997.

Knebel, t al. "Heart Failure: State-of-the-Art Treatment and New Therapeutic Options," *Clinical Nephrology*, vol. 60 (Supplement 1), pp. S59-S66, 2003.

McCarthy, Patrick M., "New Surgical Options for the Failing Heart," *Journal of Heart Valve Disease*, vol. 8, No. 5, pp. 472-475, 1999.

Shim, et al. "Step Cell Cardiomyoplasty: State-of-the-Art," *Annals of the Academy of Medicine*, Singapore, vol. 33, No. 4, pp. 451-460, 2004.

Barrett, et al. "Growth Factors for Chronic Plantar Fasciitis?" *Podiatry Today*, pp. 37-42, Nov. 2004.

Eppley, et al. "Platelet Quantification and Growth Factor Analysis from Platelet-Rich Plasma: Implications for Wound Healing," *Plastic and Reconstructive Surgery*, pp. 1502-1508, vol. 114, No. 6, Nov. 2004.

Kahn, et al. "Overuse Tendinosis, Not Tendinitis, Part 1: A New Paradigm for a Difficult Clinical Problem," *The Physician and Sportsmedicine*, vol. 28, No. 5, 8 pages, May 2000.

Cook, et al. "Overuse Tendinosis, Not Tendinitis, Part 2: Applying the New Approach to Patellar Tendinopathy," *The Physician and Sportsmedicine*, vol. 28, No. 6, 12 pages, Jun. 2000.

Khan, et al. "Histopathology of Common Tendinopathies: Update and Implications for Clinical Management," *Clinical Sports Medicine*, vol. 27, No. 6, 1999.

Price, et al. "Local Injection Treatment of Tennis Elbow—Hydrocortisone, Triamcinolone and Lignocaine Compared," *British Journal of Rheumatology*, vol. 30, pp. 39-44, 1991.

Floryan, et al. "Home Study Program: Intraoperative Use of Autologous Platelet-Rich and Platelet-Poor Plasma for Orthopedic Surgery Patients," *Aorn Journal*, vol. 80, No. 4, pp. 667-678, Oct. 2004.

Balk, et al. "Outcome of Surgery for Lateral Epicondylitis (Tennis Elbow): Effect of Worker's Compensation," *The American Journal of Orthopedics*, pp. 122-126, Mar. 2005.

Harvest Technologies GmbH Brochure for SmartPReP 2, 2002.

Cell Factor Technologies, Inc., Brochure for GPS II Platelet Concentrate System, 10 pages, 2004.

Cell Factor Technologies, Inc., Brochure for Boost Demineralizedbonematrix, 6 pages, 2004.

DePuy AcroMed, Inc. Brochure for Symphony Platelet Concentrate System, 10 pages, 2001.

Martinez-Gonzalez, et al. "Do Ambulatory-Use Platelet-Rich Plasma (PRP) Concentrates Present Risks," *Medicina Oral*, vol. 7, pp. 375-390, 2002.

Cotter, et al. "A Novel Method for Isolation of Neutrophils from Murine Blood Using Negative Immunomagnetic Separation," *The American Journal of Pathology*, vol. 159, pp. 473-481, 2001.

Yang, et al. "Dielectric Properties of Human Leukocyte Subpopulations Determined by Electrorotation as a Cell Separation Criterion," *Biophysical Journal*, vol. 76, pp. 3307-3314, Jun. 1999.

Snyder, et al. "Calcium-Dependent Proteolysis of Actin During Storage of Platelet Concentrates," *Blood*, vol. 73, No. 5, pp. 1380-1385, 1989.

Tang, et al., "The Effects of pCO2 and pH on Platelet Shape Change and Aggregation for Human and Rabbit Platelet-Rich Plasma," *Thrombosis Research*, vol. 10, No. 1, pp. 135-145, 1977.

Edwards, et al., "Autologous Blood Injections for Refractory Lateral Epicondylitis," *The Journal of Hand Surgery*, vol. 28A, No. 2, pp. 272-278, Mar. 2003.

Gruber, et al. "Platelets Stimulate Proliferation of Bone Cells: Involvement of Platelet-Derived Growth Factor, Microparticles and Membranes," *Clin. Oral Impl. Res.*, vol. 13, pp. 529-535, 2002.

Marx, et al. "Platelet-Rich Plasma, Growth Factor Enhancement for Bone Grafts," *Oran Surgery Oral Medicine Oral Pathology*, vol. 85, No. 6, pp. 638-646, Jun. 1998.

Cohan, et al., "Wound Care and Wound Healing," in *Principles of Surgery*, Chapter 8, (Seymore, et al. eds.), pp. 263-295, New York, 1999.

Taylor, et al. "The Response of Rabbit Patellar Tendons After Autologous Blood Injection," *Medicine & Science in Sports & Exercise*, vol. 34, No. 1, pp. 70-73, 2002.

Coller, et al. "The pH Dependence of Quantitative Ristocetin-Induced Platelet Aggregation: Theoretical and Practical Implications—A New Device for Maintenance of Platelet-Rich Plasma pH," *Blood*, vol. 47, No. 5, pp. 841-854, May 1976.

Rácz, et al. Buffy Coat or Platelet-Rich Plasma? *Vox Sanguinis*, vol. 47, No. 2, pp. 108-113, 1984.

Vasconcelos, et al. "Quality of Platelet Concentrates Derived by Platelet Rich Plasma, Buffy Coat and Apheresis," *Transfusion and Apheresis Science*, vol. 29, No. 1, pp. 13-16, 2003.

Vassallo, et al. "A Critical Comparison of Platelet Preparation Methods," *Current Opinion in Hematology*, vol. 13, pp. 323-330, 2006.

Edwards, et al. "Autologous Blood Injections for Refractory Lateral Epicondylitis," *The Journal of Hand Surgery*, pp. 272-278, vol. 28A, No. 2, Mar. 2003.

Bales, et al. "Microvascular Supply of the Lateral Epicondyle and Common Extensor Origin," *J. Shoulder and Elbow Surgery*, 16 94::497-501, 2007.

Chansky, et al. "The Vascularity of the Rotator Cuff," *Clinics in Sports Medicine*, 10(4):807-22, 1991.

Durukan, et al. "Acute Ischemic Stroke: Overview of Major Experimental Rodent Models, Pathophysiology, and Therapy of Focal Cerebral Ischemia," *Pharmacology, Biochemistry and Behavoir*, 87:179-197, 2007.

Playford, et al. "Combined Effect of Coenzyme Q10 and Fenofibrate on Forearm Microcirculatory Function in Type II Diabetes," *Artherosclerosis*, 168:169-179, 2003.

Neisius, et al. "Renal Oncocytoma: Diagnostic and Therapeutical Consequences," *Urologe Ausgabe A.*, 32(5):415-419, 1993.

Hinkel, "The Effect of Irradiation Upon the Composition and Vascularity of Growing Bones," *A.J. Roentgenol. and Radium Therap*, 50(4):516-526, 1943.

Pang, et al. "Clinical Implications of Angiogenesis in Cancers," *Vascular Health and Risk Management*, 2(2):97-108 (2006).

Mooar, et al. "The Efficacy of Autologous Platelet Gel Administration in Total Knee Arthroplasty: An Analysis of Range of Motion, Hemoglobin and Narcotic Requirement," Poster #148 presented at American Academy of Orthopaedic Surgeons 67$^{th}$ Annual Meeting, Orlando, FL, Mar. 15-19, 2000.

Fylling, et al. "Multi-Center Clinical Review: Using Autologous Platelet Gel for the Treatment of Diabetic Plantar Wounds," *Diabetes*, 50 (Supplement 2), A227 (Jun. 2001).

Shvets, "Local Injections of Anesthetics and Corticosteroids in the Treatment of Degenerative Changes in the Spine," *Chirugia narzadow ruchu i ortopedia polska*, 45(3):259-63, 1980.

Gawaz, et al. "Platelet Function in Acute Myocardial Infarction Treated with Direct Angioplasty," *Circulation*, vol. 93, pp. 229-237, 1996 with "Methods, Specimen Collection, Methods, Platelet Aggregation in Vitro, Discussion, Platelet Adhesion to Endothelium in AMI," downloaded from http://circ.ahajournals.org/cgi/content/full/93/2/229 on Dec. 2, 2009.

Ohman, et al. "Cardiac Troponin T Levels for Risk Stratification in Acute Myocardial Ischemia," *The New England Journal of Medicine*, vol. 335, No. 18, pp. 1333-1341, Oct. 31, 1996.

\* cited by examiner

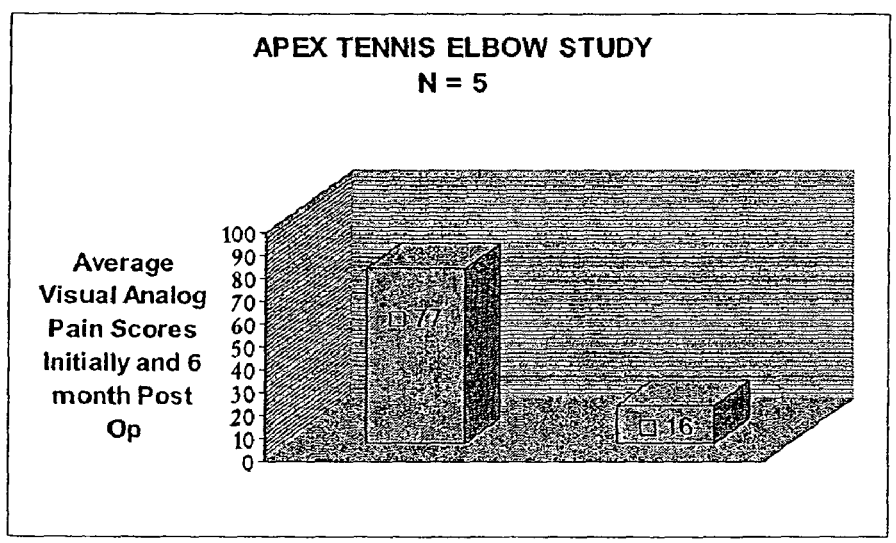
Figure 1. Decrease in average visual analog pain scores at 6 months post-op.

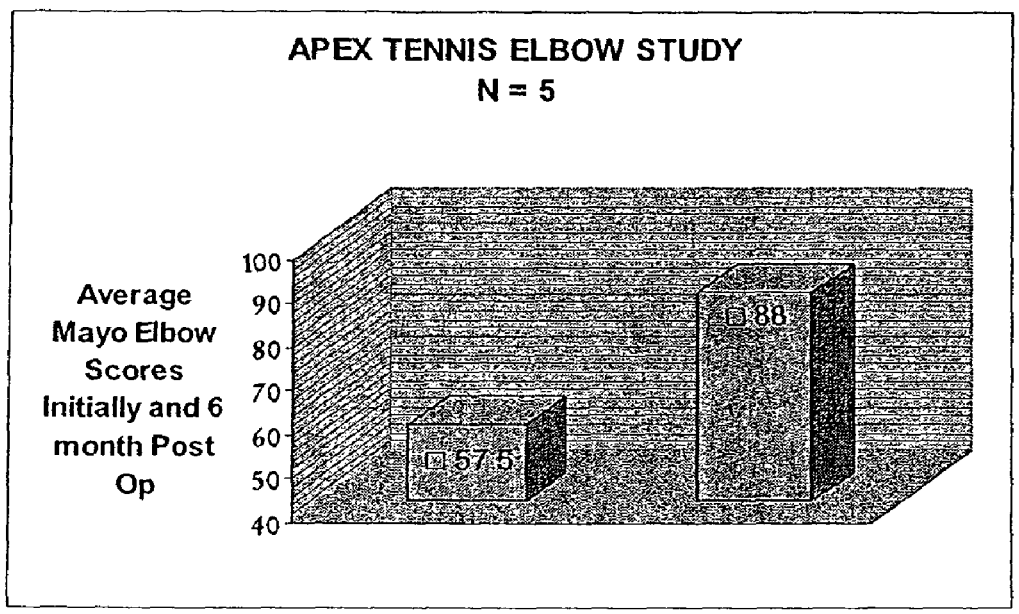
Figure 2. Mayo elbow score improvement at 6 months post-op.

KITS FOR TREATING DYSFUNCTION OF CARDIAC MUSCLE

RELATED APPLICATIONS

This application is a continuation of U.S. application Ser. No. 10/941,124, filed Sep. 15, 2004, now U.S. Pat. No. 7,314,617, which is a continuation of U.S. application Ser. No. 10/412,821, filed Apr. 11, 2003, now U.S. Pat. No. 6,811,777, which claims the priority of Provisional Application No. 60/372,682, filed Apr. 13, 2002 which are incorporated herein by reference in their entirety.

BACKGROUND OF THE INVENTION

1. Field of the Invention

In one embodiment, the present invention is directed to a method for the treatment of damaged tissue with a composition that includes platelet-rich plasma. The treated tissue may be connective tissue, cardiac muscle, skeletal muscle, disc material, vertebral bodies, pancreas and other internal organs, brain tissue or spinal cord tissue, or vascular tissue. In a preferred embodiment, the tissue is connective tissue. The described compositions and methods are also useful in wound healing and infections.

2. Description of the Related Art

There is a need for treatment protocols for connective tissue injuries which are refractory to standard treatments such as anti-inflammatory medication, bracing, rest and physical therapy. Injuries or other damage to flexible, relatively avascular connective tissues (hereafter "connective tissue" or "connective tissues") are known to take a very long time to heal (months or even years). In many cases, injuries to connective tissues may never heal properly, necessitating surgical intervention. Connective tissue injuries and disorders have a significant impact on society. The overall prevalence of these problems is approximately 140 per 1000 persons in the United States, according to a 1995 survey by the National Center for Health Statistics. The same survey estimated the direct costs to be $88.7 billion and the indirect costs estimated to be up to $111.9 billion for lost productivity.

One example of a connective tissue disorder is lateral epicondylitis. Lateral epicondylitis or "tennis elbow" is a well-known sports medicine and orthopedic disorder. The pathology underlying the disorder is related to overuse injury and microtearing of the extensor carpi radialis brevis tendon at the elbow. The body attempts to repair these microtears but the healing process is incomplete in many cases. Pathologic specimens of patients undergoing surgery for chronic lateral epicondylitis reveal a disorganized angiofibroblastic dysplasia. This incomplete attempt at repair results in degenerative, immature and avascular tissue. Incompletely repaired tissue is weaker than normal tendon tissue and lacks the strength to function normally. This tissue also limits the patient by causing pain and negatively impacting the patient's quality of life.

Similar incomplete repair may be present in other types of connective tissue injuries or damage, such as patellar tendonitis (Jumper's Knee), Achilles tendonitis (common in runners), and rotator cuff tendonitis (commonly seen in "overhead" athletes such as baseball pitchers), chronic injuries of the ankle ligaments ("ankle sprains"), or ligament tears.

The pathophysiology of the above-mentioned conditions have been studied. Presently, many different non-operative and operative treatments exist. The non-operative measures include rest, activity modification, oral anti-inflammatory medication and cortisone injections. Rest and activity modification may help patients with some of these conditions, but there remains a significant clinical population that are not reachable with these therapies. Despite widespread use, oral anti-inflammatory medications have not proven to be useful in controlled studies. Some studies further suggest that non-steroidal medication may actually have an adverse effect on the healing process for ligament injuries. Also, no acute inflammatory cells have been found in pathologic samples of cases of lateral epicondylitis. Cortisone injections are frankly controversial in the treatment of tendinoses and are contraindicated in acute ligament injuries. Several studies note an improvement in patients treated with cortisone in short term follow up. Results beyond one year, however, reveal a high symptom recurrence rate and only an equivocal efficacy rate. These injections also carry the risk of tendon rupture, infection, skin depigmentation, subdermal atrophy and hyperglycemia in diabetic patients. The operative measures include debridement and repair of the associated pathologic tendons. However, open or arthroscopic surgery has many potential complications such as deep infection, damage to neurovascular structures, and scar formation. The surgery is also expensive and carries the additional risks associated with regional or general anesthesia.

What is needed are compositions and methods for solving the problems noted above. Platelet-rich plasma (PRP) is an enriched platelet-containing mixture, isolated from whole blood, which is resuspended in a small volume of plasma. While whole blood may contain about 95% red blood cells, about 5% platelets and less than 1% white blood cells, PRP may contain 95% platelets with 4% red blood cells and 1% white blood cells. PRP can be combined with activating agents such as thrombin or calcium which activate the platelets to release their contents such as cytokinins and other growth factors. PRP has been used in medicine, primarily in bone grafting and dental implant applications and as part of a composition to use as a surgical adhesive. For example, Landesberg et al (U.S. Pat. No. 6,322,785) disclose an autologous platelet gel that includes PRP for bone grafts and dental implants. The PRP is activated by collagen and is applied topically to promote wound healing.

Antanavich et al. (U.S. Pat. No. 5,585,007) disclose preparation of PRP and use as a tissue sealant. Cochrum (U.S. Pat. No. 5,614,214) discloses a biopolymer that optionally includes PRP and its use to temporarily block arteries and veins. Gordinier et al. (U.S. Pat. No. 5,599,558) disclose a platelet releasate product, which includes platelets buffered to approximately pH 6.5, for use in a topical application to wounds.

None of the prior art teach treatment of connective tissue with PRP to promote tissue repair. Furthermore, Applicant has discovered that PRP has even broader application in treating a wide range of tissue injury and/or damage.

SUMMARY OF THE INVENTION

In one embodiment, the present invention is drawn to a method of treating an injured tissue in an individual including the steps of determining a site of tissue injury in the individual; and introducing a platelet-rich plasma composition into and around the site of tissue injury. In preferred embodiments, the tissue is selected from the group consisting of connective tissue, cardiac muscle, skeletal muscle, disc material, a vertebral body, brain, spinal cord, and vascular tissue. In a preferred embodiment, the tissue is a part of an internal organ. In a more preferred embodiment, the internal organ is the pancreas. In a particularly preferred embodiment, the tissue is a connective tissue.

In preferred embodiments the platelet-rich plasma is titrated to obtain a pH of about 7.3 to 7.5. In a more preferred embodiment, the titration is performed using a bicarbonate buffer.

In preferred embodiments, the platelet-rich plasma composition includes platelets obtained from the individual who is to be treated with the platelet-rich plasma composition. In a preferred embodiment, no exogenous activator is added to the composition prior to its introduction into and around the site of injury.

In some embodiments, the method includes the step of mixing into the platelet composition substantially simultaneously with the introduction into and around the site of tissue injury, one or more ingredients including but not limited to thrombin, epinephrine, collagen, calcium salts, and pH adjusting agents.

In one embodiment the present invention is drawn to a platelet-rich plasma composition for the treatment of an injured tissue which includes platelet-rich plasma; and a pH adjusting agent, wherein the composition does not contain an activator of the platelet-rich plasma. In a preferred embodiment, the pH of the platelet-rich plasma composition is adjusted to a pH of about 7.3 to 7.5 with a pH adjusting agent. In a more preferred embodiment, the pH adjusting agent is a bicarbonate buffer. Preferably, the plasma used for the platelet-rich plasma is from an autologous source.

In one embodiment, the present invention is drawn to a method of making a platelet-rich plasma composition including the steps of drawing blood from an individual; obtaining a plasma fraction from the blood; isolating platelets from the plasma fraction; resuspending the platelets in a reduced amount of plasma; and adjusting the pH to provide a pH of 7.3 to 7.5 for the resuspended platelets to provide a platelet-rich plasma composition, wherein an activator of the platelet-rich plasma is not added to the platelet-rich plasma composition.

BRIEF DESCRIPTION OF THE DRAWINGS

These and other feature of this invention will now be described with reference to the drawings of preferred embodiments which are intended to illustrate and not to limit the invention.

FIG. 1 shows the average visual analog pain scores at pre-op and 6 months post-op.

FIG. 2 shows the average Mayo elbow scores at pre-op and 6 months post-op.

DETAILED DESCRIPTION OF THE PREFERRED EMBODIMENT

The inventor has surprisingly discovered that certain inventive platelet compositions are useful for the treatment of several types of tissue damage or injury. As used herein, the term "injury" is a broad term and is used in the ordinary sense to refer, without limitation, to any tissue damage including a wound, trauma or lesion or any tissue degeneration. In particular, the inventive platelet compositions may be used to treat incomplete repair of various connective tissues.

In one aspect, the invention relates to a method of treating incomplete repair in a patient's connective tissue comprising: obtaining a platelet composition; determining a lesion that comprises the incomplete repair in the patient's connective tissue; and minimally invasively introducing the platelet composition into and around the lesion. In an aspect, the invention relates to the method wherein the platelet composition is at or above physiological pH. In an aspect, the invention relates to the method wherein the platelet composition optionally includes platelet releasate. In an aspect, the invention relates to the method further comprising: mixing into the platelet composition one or more of the ingredients selected from thrombin, epinephrine, collagen, calcium salts, and pH adjusting agents. Also useful are materials to promote degranulation or preserve platelets, additional growth factors or growth factor inhibitors, small molecule pharmaceuticals such as NSAIDS, steroids, and anti-infective agents. In an aspect, the invention relates to the method wherein the patient's connective tissue is selected from: tendons, ligaments, joint capsules, and fascial tissues. In an aspect, the invention relates to the method wherein obtaining the platelet composition comprises: drawing blood from a human; and centrifuging the blood to obtain a plasma-rich fraction. In an aspect, the invention relates to the method wherein the platelet composition comprises platelet-rich plasma. In an aspect, the invention relates to the method with the proviso that the platelet composition is substantially free from exogenous activators prior to its introduction into and around the region of the incomplete repair in the patient's connective tissue. In an aspect, the invention relates to the method wherein the platelet composition comprises platelets obtained from the patient.

The invention further relates to a method of treating incomplete repair in a patient's connective tissue comprising: obtaining a platelet composition; determining a lesion that comprises the incomplete repair in the patient's connective tissue; and introducing the platelet composition into and around the lesion, with the proviso that substantially no activator is added to the platelet composition prior to its introduction into and around the lesion. The invention also relates to the method wherein the platelet composition is minimally invasively introduced into and around the lesion. The invention also relates to the method wherein the platelet composition comprises platelet-rich plasma. The invention also relates to the method further comprising: mixing into the platelet composition substantially simultaneously with its minimally invasive introduction into and around the lesion one or more of the ingredients selected from thrombin, epinephrine, collagen, calcium salts, and pH adjusting agents. Also useful are materials to promote degranulation or preserve platelets, additional growth factors or growth factor inhibitors, small molecule pharmaceuticals such as NSAIDS, steroids, and anti-infective agents. The invention also relates to the method wherein the patient's connective tissue is selected from: tendons, ligaments, joint capsules, and fascial tissues. The invention also relates to the method wherein introducing the platelet composition into and around the lesion comprises activating platelets in the platelet composition through the action of collagen present in the patient's connective tissue. The invention also relates to the method wherein the platelet composition is at or above physiological pH. The invention also relates to the method wherein the platelet composition comprises platelets obtained from the patient.

In yet another aspect, the invention relates to a composition comprising: platelet releasate wherein the composition is at a pH greater than or equal to physiological pH, and wherein the composition comprises substantially no unactivated platelets.

In a further aspect, the invention relates to a method of treating lesions resulting from acute injury to or chronic disorders of the Medial Collateral Ligament of the knee or elbow, Extensor Carpi Radialis Brevis tendon, Anterior Talofibular Ligament at the ankle, Achilles tendon, posterior tibial tendon, patellar tendon, quadriceps tendon, Anterior Cruciate Ligament, Posterior Cruciate Ligament, spinal ligaments, disc materials, rotator cuff tendon, or biceps tendons comprising: obtaining a platelet composition; determining a location of the lesion; and introducing the platelet composition into and around the lesion, with the proviso that substantially no activator is added to the platelet composition prior to its introduction into and around the lesion. In an aspect, the invention relates to the method wherein the platelet composition is minimally invasively introduced into and around the lesion. In an aspect, the invention relates to the method wherein the platelet composition comprises platelet-rich plasma. In an aspect, the invention relates to the method further comprising: mixing into the platelet composition substantially simultaneously with its minimally invasive introduction into and around the lesion one or more of the ingredients selected from thrombin, epinephrine, collagen, calcium salts, pH adjusting agents. Also useful are materials to promote degranulation or preserve platelets, additional growth factors or growth factor inhibitors, small molecule pharmaceuticals such as NSAIDS, steroids, and anti-infective agents. In an aspect, the invention relates to the method wherein obtaining the platelet composition comprises: drawing blood from a human; and centrifuging the blood to obtain a plasma-rich fraction. In an aspect, the invention relates to the method wherein the platelet composition is at or above physiological pH. In an aspect, the invention relates to the method wherein the platelet composition comprises platelets obtained from the patient.

In a further aspect, the invention relates to a method of treating lesions resulting from injury or chronic disorders of cardiac muscle, skeletal muscle, organ systems, vascular tissue, disc material, spinal bodies, spinal cord, and brain tissue comprising: obtaining a platelet composition; determining a lesion in need of treatment; and minimally invasively introducing the platelet composition into and around the lesion. In an aspect, the invention relates to the method wherein the platelet composition optionally includes platelet releasate. In an aspect, the invention relates to the method further comprising: mixing into the platelet composition one or more of the ingredients selected from thrombin, epinephrine, collagen, calcium salts, and pH adjusting agents. Also useful are materials to promote degranulation or preserve platelets, additional growth factors or growth factor inhibitors, small molecule pharmaceuticals such as NSAIDS, steroids, and anti-infective agents. In an aspect, the invention relates to the method wherein obtaining the platelet composition comprises: drawing blood from a human; and centrifuging the blood to obtain a plasma-rich fraction. In an aspect, the invention relates to the method wherein the platelet composition is at or above physiological pH. In an aspect, the invention relates to the method wherein the platelet composition comprises platelets obtained from the patient.

In an aspect, the invention relates to the method wherein the patient's connective tissue is selected from : tendons, ligaments, joint capsules, and fascial tissues. In an aspect, the invention relates to the method wherein obtaining the platelet composition comprises: drawing blood from a human; and centrifuging the blood to obtain a plasma-rich fraction. In an aspect, the invention relates to the method wherein the platelet composition comprises platelet-rich plasma. In an aspect, the invention relates to the method with the proviso that the platelet composition is substantially free from exogenous activators prior to its introduction into and around the region of the incomplete repair in the patient' damaged or injured tissue. In an aspect, the invention relates to the method wherein the platelet composition comprises platelets obtained from the patient.

The inventive platelet composition may be a biocompatible composition that comprises unactivated platelets, activated platelets, platelet releasate(s), or the like. In an embodiment, the inventive platelet composition comprises platelet-rich plasma (PRP).

The term "PRP" as used herein is a broad term which is used in its ordinary sense and is a concentration of platelets greater than the peripheral blood concentration suspended in a solution of plasma, with typical platelet counts ranging from 500,000 to 1,200,000 per cubic millimeter, or even more. PRP is formed from the concentration of platelets from whole blood, and may be obtained using autologous, allogenic, or pooled sources of platelets and/or plasma. PRP may be formed from a variety of animal sources, including human sources.

Platelets are cytoplasmic portions of marrow megakaryocytes. They have no nucleus for replication; the expected lifetime of a platelet is some five to nine days. Platelets are involved in the hemostatic process and release several initiators of the coagulation cascade. Platelets also release cytokines involved with initiating wound healing. The cytokines are stored in alpha granules in platelets. In response to platelet to platelet aggregation or platelet to connective tissue contact, as would be expected in injury or surgery, the cell membrane of the platelet is "activated" to secrete the contents of the alpha granules. The alpha granules release cytokines via active secretion through the platelet cell membrane as histones and carbohydrate side chains are added to the protein backbone to form the complete cytokine. Platelet disruption or fragmentation, therefore, does not result in release of the complete cytokine.

A wide variety of cytokines are released by activated platelets. Platelet derived growth factor (PDGF), transforming growth factor-beta (TGF-b), platelet-derived angiogenesis factor (PDAF) and platelet derived endothelial cell growth factor (PD-ECGF) and insulin-like growth factor (IGF) are among the cytokines released by degranulating platelets. These cytokines serve a number of different functions in the healing process, including helping to stimulate cell division at an injury site. They also work as powerful chemotactic factors for mesenchymal cells, monocytes and fibroblasts, among others. For the purposes of this patent, the term "releasate" refers to the internal contents of the platelet, including cytokines, which have the potential to affect another cells' function.

Historically, PRP has been used to form a fibrin tissue adhesive through activation of the PRP using thrombin and calcium, as disclosed in U.S. Pat. No. 5,165,938 to Knighton, and U.S. Pat. No. 5,599,558 to Gordinier et al., incorporated in their entirety by reference herein. Activation results in release of the various cytokines and also creates a clotting reaction within various constituents of the plasma fraction. The clotting reaction rapidly forms a platelet gel (PG) which can be applied to various wound surfaces for purposes of hemostasis, sealing, and adhesion.

For instance, PG has been employed to assist with hemostasis in spine surgery and in a rat liver laceration model. One recent investigation showed that use of PG resulted in a significant reduction in post-op narcotic use, a reduction in post-op hemoglobin drop and faster return of functional range of motion after total knee replacement. PG has also been used in wound sealing. One study employed autologous PG as a sealant for craniotomy procedures and noted success in 39 out of 40 patients. PG has further been noted to augment bone healing. One controlled randomized prospective trial of 88 patients revealed a 2 fold increase in radiographic bone maturation and a 50% improvement in histologic bone density when PG was used (Marx, et al., Oral Surg. Oral Med. Oral Path. 1998, vol. 85(6): 638-646). In cardiac and vascular surgery PG is being employed to reduce the incidence of post-op wound dehiscence and infection (Kjaergard, et al., Eur J Cardio-Thoracic Surg. 1996, vol 10: 727-733; Slater, et al., J Ortho Res. 1995, vol 13: 655-663; Sumner et al. J. Bone Joint Surg. (Am) 1995, vol 77:1135-1147; Sethi, et al. Presented at International Society for the Study of Lumbar Spine, June 2001).

However, in none of the above applications and published documents has it ever been disclosed that PRP could be used surgically outside of the context of PG for any purposes other than platelet transfusions to a patient. It is one unique feature of this invention that platelets do not need to be activated prior to their introduction into a patient during the practice of the present invention.

In another embodiment, the inventive platelet composition may comprise releasate from platelets, in addition to platelets themselves. The releasate comprises the various cytokines released by degranulating platelets upon activation. Many activators of platelets exist; these include calcium ions, thrombin, collagen, epinephrine, and adenosine diphosphate. Releasates according to the invention may be prepared according to conventional methods, including those methods described in U.S. Pat. No. 5,165,938 to Knighton, and U.S. Pat. No. 5,599,558 to Gordinier et al.

One disadvantage of conventional releasate strategies associated with the use of PRP as PG is the use of thrombin as a preferred activator. In particular, much thrombin used in PG is bovine thrombin, which can create problems due to contamination issues regarding Creutzfeldt-Jakob disease. Many bovine materials are suspect due to possible prion contamination, and so use of bovine thrombin is disfavored in surgery. Human pooled thrombin is likewise disfavored due to the potential of contamination with various materials such as viruses, prions, bacteria and the like. Recombinant human thrombin might also be used, but is quite expensive.

It is a particular advantage of the present invention that exogenous or extra activators need not be administered to a patient. Collagen, a major component of connective tissues, is a strong activator of platelets. Thus, when the inventive platelet composition is introduced into and/or around connective tissue, platelets in the platelet composition may bind to the collagen and then be activated. This reduces or eliminates the need for administering an exogenous activator such as thrombin. The disadvantages of thrombin use have been noted above. Other strong activators, such as calcium ions, can cause severe pain, unintentional clotting, and other undesirable side effects. Thus, in an embodiment of the invention, no or substantially no exogenous activator is present or added as part of the inventive platelet composition, or is used in the preparation of the inventive platelet composition. Of course, exogenous activators may still be employed if a physician determines that they are medically necessary or desirable.

The platelet composition may be prepared using any conventional method of isolating platelets from whole blood or platelet-containing blood fractions. These include centrifugal methods, filtration, affinity columns, and the like. If the platelet composition comprises PRP, then conventional methods of obtaining PRP, such as those disclosed in U.S. Pat. Nos. 5,585,007 and 5,788,662 both to Antanavich et al., incorporated herein by reference in their entirety, may be utilized.

The platelet-rich plasma composition may be delivered to an individual in need thereof by convention means which include injection using a syringe or catheter. The platelet rich plasma composition may also be delivered via a dermal patch, a spray device or in combination with an ointment, bone graft or drug. It may further be used as a coating on suture, stents, screws, plates or some other implantable medical device. Finally, it may be used in conjunction with a bioresorbable drug or device.

The site of delivery of the platelet-rich plasma composition is at or near the site of tissue injury and/or damage. The site of tissue injury or damage is determined by well-established methods including imaging studies and patient feedback or a combination thereof. The preferred imaging study used is determined by the tissue type. Commonly used imaging methods include, but are not limited to MRI, X-ray, CT scan, Positron Emission tomography (PET), Single Photon Emission Computed Tomography (SPECT), Electrical Impedance Tomography (EIT), Electrical Source Imaging (ESI), Magnetic Source Imaging (MSI), laser optical imaging and ultrasound techniques. The patient may also assist in locating the site of tissue injury or damage by pointing out areas of particular pain and/or discomfort.

Adjusting the pH of platelet compositions has been used to prolong the storage time of unactivated platelets, as disclosed in U.S. Pat. No. 5,147,776 to Koerner, Jr. and U.S. Pat. No. 5,474,891 to Murphy, incorporated by reference herein. pH may be adjusted using a variety of pH adjusting agents, which are preferably physiologically tolerated buffers, but may also include other agents that modify pH including agents that modify lactic acid production by stored platelets. Especially useful are those pH adjusting agents that result in the pH of the platelet composition becoming greater than or equal to physiological pH. In an embodiment, the pH adjustment agent comprises sodium bicarbonate. Physiological pH, for the purposes of this invention, may be defined as being a pH ranging from about 7.35 to about 7.45. pH adjusting agents useful in the practice of this invention include bicarbonate buffers (such as sodium bicarbonate), calcium gluconate, choline chloride, dextrose (d-glucose), ethylenebis(oxyethylenenitrilo)tetraacetic acid (EGTA), 4-(2-hydroxyethyl)-1-piperazineethanesulfonic acid (HEPES), maleic acid, 4-morpholinepropanesulfonic acid (MOPS), 1,4-piperazinebis (ethanesulfonic acid) (PIPES), sucrose, N-tris (hydroxymethyl)methyl-2-aminoethanesulfonic acid (TES), tris(hydroxymethyl)aminomethane (TRIS BASE), tris(hydroxymethyl)aminomethane hydrochloride (TRIS.HCl), and urea. In a preferable embodiment, the pH adjusting agent is a bicarbonate buffer, more preferably, sodium bicarbonate.

For the purposes of this patent, the term "tissues" includes but is not limited to cardiac and skeletal muscle, disc material, vertebral bodies, internal organs, brain and spinal cord tissue, vascular tissue such as arteries and veins and non-differentiated tissue.

For the purposes of this patent, connective tissues comprise tendons, ligaments, fascial tissues, and joint capsules. In a preferable embodiment, connective tissues comprise the Medial Collateral Ligament of the knee or elbow, Extensor Carpi Radialis Brevis tendon (tennis elbow), Anterior Talofibular Ligament at the ankle, Achilles tendon, Anterior Cruciate Ligament, Posterior Cruciate Ligament, posterior tibial tendon, patellar tendon, quadriceps tendon, rotator cuff tendon, and biceps tendons.

Incomplete repair, as it is used in the context of this patent application, may be defined to mean repair that is disorganized, substantially non-existent (such as in the case of an unhealed tear), or otherwise pathological. Disorganized repair is characterized by a disorganized angiofibroblastic dysplasia, with degenerative, immature and avascular tissue. Such tissue is weaker than normal connective tissue and lacks the strength to function normally. This tissue also limits the patient by causing pain and negatively impacting the patient's quality of life. Substantially non-existent repair might occur in a situation where a connective tissue is torn and does not heal properly subsequently to the tear. Otherwise pathological repair may be any other type of repair in which the tissue is not repaired to be substantially the same as the tissue was before tissue repair was necessary.

It will be apparent to those skilled in the art that various modifications and variations can be made to the present invention without departing from the spirit or scope of the invention. Thus, it is intended that the present invention cover the modifications and variations of the present invention provided that they come within the scope of the appended claims and their equivalents. The following examples are illustrative of the present invention, and are not intended to limit it.

EXAMPLES

Example 1

PRP was prepared using a centrifuge unit made by Harvest (Plymouth, Mass.). (Similar units are available as The Biomet GPS system, the Depuy Symphony machine and the Medtronic Magellan machine.) Approximately 55 cc of blood was drawn from the patient using a standard sterile syringe, combined with 5 cc of a citrate dextrose solution for anticoagulation, and then spun down to isolate the platelets according to the manufacturer's protocol. These platelets were then resuspended in approximately 3 cc of plasma. The resulting platelet rich plasma solution (PRP) was quite acidic and was neutralized with using approximately 0.05 cc of an 8.4% sodium bicarbonate buffer per cc of PRP under sterile conditions to approximately physiologic pH of 7.4. The PRP was not activated through addition of exogenous activators. This PRP composition is referred to herein as autologous platelet extract (APEX).

Example 2

Fifty cc of whole blood is drawn from a patient, and then prepared according to the method of Knighton, U.S. Pat. No. 5,165,938, column 3. The PRP is activated according to Knighton using recombinant human thrombin. The degranulated platelets are spun down and the releasate containing supernatant is recovered. The releasate may be optionally pH adjusted to a pH of 7.4 using sodium bicarbonate buffer.

Example 3

Thirty ml of whole blood were drawn from a patient. A platelet composition was prepared according to Example 1 of U.S. Pat. No. 5,510,102 to Cochrum, incorporated herein by reference in its entirety, except that no alginate is added to the platelet composition.

Example 4

A study of the effects of the PRP compositions described herein was done using patients presenting with lateral epicondylitis (tennis elbow) which had failed non-operative treatment (anti-inflammatory medication, bracing rest and physical therapy). The average duration of symptoms of these patients was 16.6 months. After obtaining informed consent, the patients were formally enrolled in the study and randomly assigned to either the APEX treatment group or control.

The patients were evaluated to obtain a visual pain score, a Mayo Elbow Score, and grip strength. For the visual analog pain score, zero equals "no pain" and 100 equals "the worst pain possible." The Mayo elbow score is an overall function score with a higher score indicating better overall function. The values of the two scores were statistically evaluated using a paired sample T test with significance set at $p<0.05$.

Each patient was then given 5 mg of Valium p.o. 30 minutes prior to the inventive tendon procedure. Patients were then prepped and draped in a sterile manner. A local anesthetic of 0.5% bupivicaine with epinephrine was infiltrated into the skin, subcutaneous structures and extensor carpi radialis brevis tendon. Care was taken to keep the local anesthetic out of the elbow joint.

Two to three minutes after administration of the local anesthetic, approximately 3-5 cc of the APEX composition of Example 1 was introduced into the extensor carpi radialis brevis tendon at the elbow via a 22 gauge needle. The control group received a numbing shot (Bupivicaine). Multiple punctures into the tendon approximately 0.5-1 cm from its origin were made. Promptly after the minimally invasive introduction of either the APEX composition of Example 1 or the numbing shot, the patient's arm was immobilized at about 90% of flexion without elevation of the arm or hand. The surgical area was then sterilely dressed and the patient asked not to move their arm for 30 minutes. Each patients' neurovascular, pain and function status was evaluated shortly after the injection, and at 30 minutes following the end of the procedure. Each patient was given oral narcotic pain medication as needed for the first 24-48 hours after the procedure. A formal postoperative stretching and strengthening program may be initiated at 2-3 days after the procedure. The visual pain score, Mayo Elbow Score, and grip strength were all monitored post-procedure.

Tables 1 and 2 compare treated patients and control preoperatively and at 8 weeks. 5 patients have been treated with the PRP compositions of one aspect of the present invention (APEX) while 3 patients received a numbing shot and provided a control. The visual analog pain scores (Table 1) improved an average of 66% for the PRP-treated group versus an average improvement of 20.4% in the control group. The MAYO elbow score (Table 2) which tests elbow function improved by an average of 44% in the PRP-treated group compared to 30.5% in the control group.

TABLE 1

TENNIS ELBOW STUDY.
Averaged Visual Analog Pain Scores (0-100) for 5 patients treated with APEX and 3 control patients preoperatively and at 8 week follow-up.

|  | APEX | Control (Bupivicaine) |
|---|---|---|
| Preoperative | 77 | 90 |
| Postoperative-8 weeks | 26 | 72 |
| % improvement | 66% | 20.4% |
| n | 5 | 3 |

TABLE 2

TENNIS ELBOW STUDY.
Averaged Mayo Elbow Scores for 5 patients treated with APEX and 3 control patients preoperatively and at 8 week follow-up.

|  | APEX | Control (Bupivicaine) |
|---|---|---|
| Preoperative | 57.5 | 49 |
| Postoperative-8weeks | 83 | 64 |
| % improvement | 44% | 30.5% |
| n | 5 | 3 |

The improvement seen in the control may be attributed to the observed phenomenon that insertion of a needle into a painful area without drug delivery (dry needling), will result in some relief from pain symptoms. However, the significantly larger improvements in elbow function (Table 2) and pain level (Table 1) clearly demonstrate the efficacy of the PRP treatments that are an aspect of the present invention.

Example 5

The patient sample of Example 4 was again evaluated at 6 month time points. To date, five patients that are at least six months post treatment with the APEX composition using the inventive method described herein have been evaluated. The results are outlined below in Tables 3 and 4. Average values for 5 patients tested so far are shown.

TABLE 3

VISUAL ANALOG PAIN SCORE

| | |
|---|---|
| Preoperative Visual Analog Pain Score Average: | 77 |
| Six Month Postoperative Visual Analog Pain Score Average: | 16 |
| Improvement | 79% |

TABLE 4

MODIFIED MAYO ELBOW SCORE (A measure of overall function)

| | |
|---|---|
| Preoperative Visual Analog Pain Score Average: | 57.5 |
| Six Month Postoperative Mayo Elbow Score Average: | 88 |
| Improvement | 53% |

The Visual Analog Pain Score (Table 3) represents an average of 79% improvement in pain scores at six months. Table 4 represents an average of 53% improvement in Mayo Elbow score at six months. The data is graphically depicted in FIG. 1 (visual analog pain scores) and FIG. 2 (Mayo elbow score improvement). Importantly, 4 of 5 patients are excellent (>90 by Mayo elbow score) and one patient is in the good category. All patients were either fair or poor prior to treatment. Even with this small sample, the improvement was statistically significant (p values=<0.05).

Example 6

A patient presenting with Achilles tendinosis is given 5 mg of Valium p.o. 30 minutes prior to the inventive tendon procedure. The patient is then prepped and draped in a sterile manner. A local anesthetic of 0.5% bupivicaine with epinephrine is infiltrated into the skin, subcutaneous structures and Achilles tendon. Care is taken to keep the local anesthetic out of the ankle joint.

Two to three minutes after administration of the local anesthetic, approximately 3-5 cc of the APEX composition of Example 1 is introduced into the Achilles tendon just above the ankle via a 22 gauge needle. Multiple punctures into the tendon approximately 0.5-1 cm from its insertion are made. Promptly after the minimally invasive introduction of the platelet composition of Example 1, the patient's lower leg and foot are immobilized without elevation of the leg. The surgical area is then sterilely dressed and the patient is asked not to move their leg for 30 minutes. The patient's neurovascular, pain and function status is evaluated shortly after the injection, and at 30 minutes following the end of the procedure. The patient is given oral narcotic pain medication as needed for the first 24-48 hours after the procedure. The Achilles tendon remains immobilized for one week following the procedure, followed by an formal postoperative stretching and strengthening program initiated at 8-10 days after the procedure.

Example 7

A patient presenting with a medial collateral ligament tear of the elbow is given 5 mg of Valium p.o. 30 minutes prior to the inventive tendon procedure. The patient is then prepped and draped in a sterile manner. A local anesthetic of 0.5% bupivicaine with epinephrine is infiltrated into the skin, subcutaneous structures and medial collateral ligament at the elbow. Care is taken to keep the local anesthetic out of the elbow joint.

Two to three minutes after administration of the local anesthetic, approximately 3-5 cc of the APEX composition of Example 1 is introduced into the medial collateral ligament at the elbow via a 22 gauge needle. Multiple punctures into the ligament approximately 0.5-1 cm from its origin are made. Promptly after the minimally invasive introduction of the platelet composition of Example 1, the patient's elbow and arm are immobilized at about 90% of flexion without elevation of the arm or hand. The surgical area is then sterilely dressed and the patient is asked not to move their arm for 30 minutes. The patient's neurovascular, pain and function status is evaluated shortly after the injection, and at 30 minutes following the end of the procedure. The patient is given oral narcotic pain medication as needed for the first 24-48 hours after the procedure. An optional formal post-operative stretching and strengthening program may be initiated at 2-3 days after the procedure.

Example 8

Cardiac Muscle

A patient presents with either an acute (i.e. heart attack) or chronic dysfunction (i.e. congestive heart failure) of cardiac muscle. An APEX composition is prepared as described in Example 1 Approximately 0.05 cc of an 8.4% sodium bicarbonate buffer per cc of extract is used to raise the pH to or slightly above 7.4. The extract is not activated through the addition of exogenous agent(s).

The APEX is then introduced into the area of dysfunctional cardiac muscle via a catheter. The APEX may also be combined with an implantable device such as a stent.

Example 9

Skeletal Muscle

A patient presents with weakness or atrophy of skeletal muscle. This could be the result of an injury or after a surgical procedure. Using the technique of Example 1, an autologous platelet extract (APEX) is obtained and buffered to physiologic pH.

The area of weakness or atrophy is identified and then after using 0.5% bupivicaine with epinephrine as a local anesthetic, the APEX is introduced into the muscle via a 22 g needle. This can be done a single time or it may require multiple injections. Postoperatively, the patient is started on a site specific stretching and strengthening protocol.

Example 10

Disc Material/Vertebral Bodies

A patient presents with low back pain and either bulging or black discs on an MRI scan. Using the technique of Example 1, an autologous platelet extract (APEX) is obtained and buffered to physiologic pH.

The disc in question is identified by X-ray guidance and then the APEX is introduced into the disc space via small gauge catheter. This procedure could be done alone or in combination with a thermal/radiofrequency ablation procedure. The APEX could also be injected into a vertebral body that has sustained a compression fracture with or without the use of a balloon prior to injection.

Example 11

Pancreas/Any Internal Organ

A patient presents with diabetes and poor insulin production. Using the technique of Example 1, an autologous platelet extract (APEX) is obtained and buffered to physiologic pH.

Under CT guidance and conscious sedation, the APEX is introduced via a small gauge catheter into the pancreas. The APEX is then injected into the islet cells to stimulate repair of these cells and thus restore insulin production.

Example 12

Brain/Spinal Cord

A patient presents with an acute neurologic deficit such as a spinal cord injury or stroke. Using the technique of Example 1, an autologous platelet extract (APEX) is obtained and buffered to physiologic pH.

Under MRI guidance and conscious sedation, the APEX is introduced into the area of injury or deficit. The APEX initiates or assists with repair of the locally damaged cells.

Example 13

Vascular Tissue

A patient presents with an area of hypovascularity in his or her lower extremities. The patient has a diagnosis of peripheral vascular occlusive disease. Using the technique of Example 1, an autologous platelet extract (APEX) is obtained and buffered to physiologic pH.

The area of hypovascularity is blocked with bupivicaine and then the APEX is introduced into either the muscle or soft tissue. The APEX induces angiogenesis and new blood vessel formation.

Example 14

Wound Healing

A patient presents with a chronic wound that is not healing properly. This could be a diabetic foot ulcer. Using the technique of Example 1, an autologous platelet extract (APEX) is obtained and buffered to physiologic pH.

The wound is carefully cleansed and debrided as needed. The APEX is then carefully injected into and around the chronic wound and its edges. It is held in place with an occlusive bandage or combined with an ointment. This process may be repeated as needed until the wound has healed.

Example 15

Neoplastic Tissue

A patient presents with either a benign or malignant tumor or process. Using the technique of Example 1, an autologous platelet extract (APEX) is obtained and buffered to physiologic pH. The APEX can be used either in vivo or in vitro to initiate or induce tumor cell death.

Specifically, the APEX is injected into a solid tumor with CT or MRI guidance via a small catheter. Alternatively, cancer cells after being grown in an APEX media could be reintroduced back into the body to attack and kill the remaining tumor. Without intending to be limited by theory, it is hypothesized that the APEX media has either the ability to cause tumor cell apoptosis (cell death) in vivo or it may have the ability to transform cancer cells into normal cells.

Example 16

Infections

A patient presents with a superficial or deep infection. Using the technique of Example 1, an autologous platelet extract (APEX) is obtained and buffered to physiologic pH.

The area of the infection is identified and the APEX is then directly applied or percutaneously introduced. This could be done under local or general anesthesia and with or without imaging guidance. The APEX typically has a concentrated number of white blood cells along with platelets. This combination of white blood cells and platelets either controls or eliminates an infection.

Example 17

Cell Cultures of Any Tissue

A researcher or clinician wishes to grow a cell culture of either fibroblasts or osteoarthritic cartilage cells. Using the technique of Example 1, an autologous platelet extract (APEX) is obtained and buffered to physiologic pH.

The cells are then isolated and grown in a media rich in the APEX in various conditions and dilutions. The APEX promotes cell differentiation and production of proteins such as collagen. The APEX may augment or promote the ability of the cells to transform into normal cells. Without intending to be limited by theory, it is hypothesized the APEX may convert the osteoarthritic cartilage cells to a more functional cell line that is reinjected into a diseased or injured joint. Alternatively, the APEX is directly introduced into an osteoarthritic joint to reverse the course of the disease. This is done under local anesthesia in a sterile manner.

Finally, the APEX may be used to help grow and differentiate any tissue or cell line in vivo or in vitro.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A delivery system for treating acute or chronic dysfunction of cardiac muscle comprising:
    a platelet-rich plasma composition comprising platelet-rich plasma and a pH adjusting agent; and
    a catheter for delivery of the platelet-rich plasma composition to dysfunctional cardiac muscle,
    wherein the platelet-rich plasma composition does not contain an activator of the platelet-rich plasma.

2. The delivery system of claim 1, wherein the pH adjusting agent provides a pH of about 7.3 to 7.5.

3. The delivery system of claim 1, wherein the pH adjusting agent is a bicarbonate buffer.

4. The delivery system of claim 1, wherein a plasma used for the platelet-rich plasma is from an autologous source.

5. The delivery system of claim 1, further comprising an implantable device.

6. The delivery system of claim 5, wherein the implantable device is a stent.

7. A kit for treating acute or chronic dysfunction of cardiac muscle comprising:
    a syringe for withdrawing blood from a patient;
    a centrifuge device to obtain platelet-rich plasma;
    a pH adjusting agent for the platelet-rich plasma to provide a platelet-rich composition having a pH of about 7.3 to 7.5; and
    a catheter for delivery of the platelet-rich plasma composition to dysfunctional cardiac muscle,
    wherein the kit does not contain an activator of the platelet-rich plasma.

8. The kit of claim 7, wherein the pH adjusting agent is a bicarbonate buffer.

* * * * *

UNITED STATES PATENT AND TRADEMARK OFFICE
CERTIFICATE OF CORRECTION

PATENT NO. : 8,163,277 B2
APPLICATION NO. : 11/494166
DATED : April 24, 2012
INVENTOR(S) : Allan Mishra It is certified that error appears in the above-identified patent and that said Letters Patent is hereby corrected as shown below:

Title Page 2, item [56]: Column 1, Line 22, ""Step Cell Cardiomyoplasty:" should be changed to --"Stem Cell Cardiomyoplasty:--

Page 2, Column 2, Line 8, "*Oran Surgery Oral Medicine*" should be changed to --*Oral Surgery, Oral Medicine*--

Page 2, Column 2, Line 37, "*and Behavoir,*" should be changed to --*and Behavior,*--

Page 2, Column 2, Line 41, "*Artherosclerosis,*" should be changed to --*Atherosclerosis,*--

Page 2, Column 2, Line 47, "ofAngiogenesis" should be changed to --of Angiogenesis--

Page 2, Column 2, Line 58, "*Chirugia*" should be changed to --*Chirurgia*--

Column 5, Line 62, "in the patient'" should be changed to --in the patient's--

Column 9, Line 20, "as The Biomet" should be changed to --as the Biomet--

Signed and Sealed this
Eleventh Day of September, 2012

David J. Kappos
*Director of the United States Patent and Trademark Office*